US010335233B2

(12) United States Patent
Sabado et al.

(10) Patent No.: US 10,335,233 B2
(45) Date of Patent: Jul. 2, 2019

(54) MYOMA/POLYP IN-OFFICE TREATMENT WITH LASERS

(71) Applicants: Martin Sabado, Cambridge (GB); Wolfgang Neuberger, Dubai (AE)

(72) Inventors: Martin Sabado, Cambridge (GB); Wolfgang Neuberger, Dubai (AE)

(73) Assignee: Biolitec Unternehmensbeteilligungs II AG, Vienna (AT)

( * ) Notice: Subject to any disclaimer, the term of this patent is extended or adjusted under 35 U.S.C. 154(b) by 745 days.

(21) Appl. No.: 13/931,210

(22) Filed: Jun. 28, 2013

(65) Prior Publication Data

US 2015/0005577 A1 Jan. 1, 2015

(51) Int. Cl.

| A61B 18/22 | (2006.01) |
|---|---|
| A61B 1/303 | (2006.01) |
| A61B 8/08 | (2006.01) |
| A61B 1/018 | (2006.01) |
| A61B 18/00 | (2006.01) |
| A61B 17/42 | (2006.01) |
| A61B 18/20 | (2006.01) |

(52) U.S. Cl.
CPC .............. *A61B 18/22* (2013.01); *A61B 1/303* (2013.01); *A61B 8/085* (2013.01); *A61B 1/018* (2013.01); *A61B 2017/4216* (2013.01); *A61B 2018/00559* (2013.01); *A61B 2018/00589* (2013.01); *A61B 2018/00625* (2013.01); *A61B 2018/00982* (2013.01); *A61B 2018/2005* (2013.01); *A61B 2018/2025* (2013.01)

(58) Field of Classification Search
None
See application file for complete search history.

(56) References Cited

U.S. PATENT DOCUMENTS

| 6,024,743 A * | 2/2000 | Edwards | A61B 18/00 606/31 |
|---|---|---|---|
| 7,063,694 B2 * | 6/2006 | Nahen | A61B 18/22 128/898 |
| 2003/0130575 A1 * | 7/2003 | Desai | A61B 8/0841 600/417 |
| 2007/0122096 A1 * | 5/2007 | Temelkuran | A61B 18/201 385/126 |

(Continued)

*Primary Examiner* — Alexandra L Newton
(74) *Attorney, Agent, or Firm* — Bolesh J Skutnik; BJ Associates

(57) ABSTRACT

A noninvasive treatment of uterine growths such as myomas (fibroids) and polyps is presented. Treatment involves carrying out diagnostic hysteroscopy and ultrasound procedures to detect, measure, and evaluate unwanted uterine growths; then inserting optical fiber into a hysteroscope, reaching target tissue with optical fiber and eliminating said tissue or shrinking it to a size/shape for easy mechanical removal. Finally, ultrasound imaging is used to confirm success of procedure. In one embodiment, optical fiber has an off-axis firing end but can be inserted inside a conventional hysteroscopy device. In another embodiment, a laser interstitial thermal therapy (LITT) fiber is used to treat myomas found on the outside of the uterus. A high energy laser is used that can emit at wavelengths easily absorbed by water and blood, such as 980 nm and 1470 nm. Procedure is fast and can be done in the physician's office with little or no anesthesia used.

7 Claims, 3 Drawing Sheets

(56) References Cited

U.S. PATENT DOCUMENTS

2008/0255498 A1* 10/2008 Houle .................... A61C 17/02
604/20
2011/0276038 A1* 11/2011 McIntyre ......... A61B 17/00234
606/1

* cited by examiner

MYOMA/POLYP IN-OFFICE TREATMENT WITH LASERS

DOMESTIC PRIORITY UNDER 35 USC 119(e)

This application claims the benefit and priority of U.S. Provisional Application Ser. No. 61/746,946 filed Dec. 28, 2012, entitled "Myoma/Polyp In-Office Treatment with Lasers" by Martin Sabado and Wolfgang Neuberger, which are incorporated by reference herein.

BACKGROUND OF THE INVENTION

1. Field of the Invention

The invention relates to the field of treatment of gynecological conditions and in particular for minimally invasive laser treatment of uterine growths, including myopias, polyps and adhesions, which can be treated in an office environment.

2. Information Disclosure Statement

Uterine growths such as myomas (fibroids) and adhesions can cause different types of complications to women, including discomfort, acute pain, anemia and inability to achieve pregnancy.

A uterine fibroid or myoma is a benign tumor that originates from the smooth muscle layer and the accompanying connective tissue of the uterus. It often appears during the childbearing years and is especially common in older women. Myomas are the most frequent pathologies in the uterine body and appear in 20-25% of women of reproductive age. As many as 3 out of 4 women have uterine fibroids sometime during their lives, but most are unaware of them because they often cause no symptoms. They may be discovered during a pelvic exam, a prenatal ultrasound exam or during hysteroscopy.

While many fibroids are asymptomatic, in many cases they can grow and cause heavy and painful menstruation, painful sexual intercourse, and urinary frequency and urgency. Some fibroids may interfere with pregnancy by distorting or blocking the fallopian tubes, or interfering with the passage of sperm from the cervix to the fallopian tubes. Fibroids can be in the cavity (submucous), in the muscle (intramural) or on the outside surface (subserosal) of the uterus. If a submucosal fibroid significantly distorts the cavity of the womb, it may prevent implantation and growth of an embryo. In some cases, fibroid tumors can grow out of the uterus on a stalk-like projection. If the fibroid twists on this stalk, it may cause sudden, sharp, severe pain in the lower abdomen. The Wamsteker classification divides myomas in three types:

G 0: myoma is completely within the uterine cavity
G I: myoma has an intramural extension of less than 50%
G 2: myoma has an intramural extension of more than 50%

Once fibroids are removed, those particular fibroids cannot grow back. But, there can be small fibroids that cannot be seen or felt, and therefore cannot be removed. These fibroids that are left behind can grow, and new ones can form.

Polyps are benign cervical fingerlike growths on the lining of the cervix. Some cervical cancers may first appear as a polyp. They can also interfere with implantation of an embryo and also may increase the risk of miscarriage.

Intra uterine scar tissue (adhesions) can develop inside the uterus from a prior pregnancy, a prior surgical procedure or a prior infection. They can obliterate or distort the uterine cavity, thus preventing the implantation of a fertilized egg or causing recurrent miscarriages.

A variety of approaches have been attempted for treatment of mentioned medical conditions.

Medication can be used to induce temporary menopause and reduce blood supply to the fibroids. This causes some shrinkage of fibroids. However, it is only a temporary solution as fibroids recover their size once medication is stopped. Furthermore, pharmacologic therapy may cause side effects, such as hot flashes, vaginal dryness, mood changes and bone density loss. Thus, pharmacologic therapy is relatively ineffective and palliative rather than curative.

Uterine artery embolization is a procedure in which tiny particles are injected through blood vessels to block the arteries supplying fibroids. This causes degeneration of the fibroids but only decreases their size and symptoms to about 50%. Side effects of this procedure include pelvic infection, premature menopause, and severe pelvic pain. Furthermore, such treatment is contraindicated on women who still wish to bear children.

Removal of the uterus (Hysterectomy) is currently the only treatment that guarantees no further menstrual bleeding and no recurrence of fibroids. This, of course, is not an option for women who do not want to become infertile. Furthermore, this procedure has the risk of many related complications, including hormonal imbalance, post-operative bleeding, vaginal prolapse, urinary tract infections, weight gain, abdominal pains, and constipation to name a few. Finally, the procedure is costly, requires a long recovery time and morbidity risk such as injury to other organs is higher than with other less invasive approaches.

Myomectomy is the surgical removal of the fibroids from the uterine muscle while trying to preserve the uterus, fallopian tubes and ovaries. It is a specialized operation done by reproductive surgeons who need to have considerable experience to preserve the uterus for future fertility. The purpose of myomectomy is to restore the uterus to normal function. Fibroids can be removed by Operative Hysteroscopy, Operative Laparoscopy or an Abdominal Myomectomy (open surgery).

An abdominal myomectomy is the removal of fibroids through an incision in the abdomen. By means of this procedure, surgeon can feel the uterus and thus find fibroids deep inside the uterus. However, abdominal myomectomy requires an incision, so recovery is longer than required if an incision is avoided. Potential for future hernias also increase after such surgeries. Women usually need to stay in hospital 48 hours after surgery before they can go home. Additionally, they need to wait up to 6 weeks before they can return to work. Finally, as scars remain in uterus, future pregnancies may be negatively affected.

Laparoscopic myomectomy is advantageous over abdominal myomectomy as several small incisions are used rather than one larger incision. Postoperative recovery is faster. However, laparoscopy is limited by the lack of wrist-like movements of currently available instruments. Additionally after laparoscopic removal of deep or multiple myomas, the uterus cannot always be repaired such that future pregnancies are successful. Furthermore, laparoscopic myomectomy also requires several weeks of rest for total recovery. The potential of future hernias is reduced but still is present.

Robotic myomectomy overcomes some disadvantages of conventional laparoscopic myomectomy and abdominal myomectomy. With a surgical robot it is possible to operate precisely through small incisions. Surgeon sits at a console and looks through a 3D video camera. The hand movements by the surgeon are duplicated in the patient by the robot, as the instruments duplicate the wrist movements of the surgeon. A robotic surgical device, however, is a very expensive instrument and requires extensive training before a surgeon can use it effectively. It still requires substantial ability to work delicately, and surely. Furthermore, this procedure still requires a long recovery period.

Noninvasive approaches have been studied, such as using cryotherapy for treatment of fibroids or using high-intensity externally-focused ultrasound (HIFU). However, initial studies of the feasibility of using cryotherapy for treatment of fibroids demonstrated an overall reduction in fibroid size of only 10%. Furthermore, control of the freezing zone can be problematic. United States application publication US20070255267A1, by Diederich et al., discloses using ultrasound energy to heat or ablate the fibroid or a portion of the fibroid. However, long treatment times are required to treat even small tissue volumes, access to fibroids located in proximity to bowel or bladder is limited, and lack of adequate acoustic window and pre-focal heating limits this technology to accessible small fibroids. Additionally, complications have been reported, such as thermal damage in deep tissue, bowel, and superficial tissue layers.

A preferred noninvasive approach to uterine conditions such as myomas is by means of hysteroscopy. A hysteroscope is an endoscope that carries optical and light channels or fibers. It is introduced in a sheath that provides an inflow and outflow channel for insufflation of the uterine cavity. In addition, an operative channel may be present to introduce scissors, graspers or biopsy instruments.

During diagnostic hysteroscopy the hysteroscope is used just to observe the inside of the uterus by means of a thin fiber optic camera. Hysteroscope is inserted through the cervix and there is no need for incisions. Detected growths such as myomas can be treated using a specific hysteroscope by ablating or resecting uterine tissue. Hysteroscopic myomectomy currently represents the standard minimally invasive surgical procedure for treating submucous fibroids. Submucous intracavitary myomas can often be removed through the cervix using a resectoscope.

In some treatments, the hysteroscope is used as a special type of resectoscope with a built-in wire loop that uses high-frequency electrical energy to cut or coagulate tissue. Although it is a minimally invasive outpatient procedure, and mostly done as an outpatient procedure; it is done under general anesthesia, thus requiring longer recovery times. It is further limited, however, in that the myomas decrease but do not totally disappear. Therefore, they can grow back again with time. Electrical energy electrodes also present the potential danger of random passage of electricity through body structures. Another disadvantage, related to the use of this type of energy, is that it produces numerous gas bubbles which may enter the vascular system. A constant monitoring of patient's end-tidal $CO_2$ together with a close cooperation between surgeon and anesthesiologist is needed to avoid serious complications. This renders treatment more complex and expensive. Additionally, resection is sometimes not well tolerated due to electrical energy transmitted to the myometrium when the active electrode gets in contact with it, causing pain and uterine contraction. Finally it is currently only possible to ambulatorily treat small, completely submucous myomas (type G 0) with this technique.

Laser technology has also been used in hysteroscopic procedures. U.S. Pat. No. 5,647,867 by Neuberger et al, discloses a surgical device to be used with standardly available resectoscopes, combining the better qualities of familiar tissue scraping tools and real time imaging with the better qualities of laser radiation surgery. Device allows for ablating and coagulating tissue using laser radiation together with scraping and cauterizing tissue and simultaneously using real time imaging capabilities. Such device is specially designed for urologic applications such as treatment of enlarged prostates. Argon, Krypton and Nd:YAG lasers have all been tried. Among these, only Nd:YAG lasers have found some application in hysteroscopic surgery. Nd:YAG lasers delivering output with a wavelength of 1064 nm have been used for ablation of the endometrium. However, 1064 nm light is poorly absorbed in blood and uterine tissue and is therefore inefficient for ablation procedures. U.S. Pat. No. 7,063,694B2 by Nahen et al. discloses delivering laser radiation to the treatment area, by vaporizing, incising, or coagulating uterine tissue, using a laser that generates light with an average power greater than 40 watts and a wavelength between 300 and 700 nm where the output beam of the laser is delivered to the target tissue through an end-firing or a side-firing optical fiber guided into the uterine cavity using a hysteroscope. In other embodiments, the wavelength of the delivered radiation is between 1100 and 1800 nm. Other embodiments employ a laser system, that generates light of two wavelengths, with for example two lasers arranged to fire between 300 and 700 nm, such as a wavelength of 532 nm, and the light of the second wavelength having a wavelength of 1064 nm. None of these embodiments have proven to be fully effective and the laser equipment used tends to be very expensive, especially embodiments referring to using combinations of laser sources. Additionally, anesthetic techniques, such as paracervical block, regional or even general anesthesia are always needed for this procedure.

Procedures discussed in the prior art fail to achieve safe, effective and low-cost removal of uterine growths such as myomas grade 0, 1 and 2 with minimum side effects and preventing fertility. The present invention addresses these needs.

Objectives and Brief Summary of the Invention

It is an objective of the present invention to provide an improved method for treatment of uterine growths such as myomas, polyps and adhesions.

It is another objective of the present invention to provide an in-office treatment of uterine growths that is non-invasive and can preserve female fertility It is still another objective of the present invention to use laser energy as a safe and effective, low-cost hysteroscopic treatment of uterine myomas.

Briefly stated, a noninvasive treatment of uterine growths such as myomas (fibroids) and polyps is disclosed. Treatment involves carrying out diagnostic hysteroscopy and ultrasound procedures to detect, measure, and evaluate unwanted uterine growths; then inserting optical fiber into a hysteroscope, reaching target tissue with optical fiber and eliminating said tissue or shrinking it to a size/shape for easy mechanical removal. Finally, ultrasound imaging is used to confirm success of procedure. In a preferred embodiment, optical fiber is designed such that it has an off-axis firing end but can be inserted inside a conventional hysteroscopy device. In another proffered embodiment, a laser interstitial thermal therapy (LITT) fiber is used to treat myomas found on the outside of the uterus. A high, energy laser is used that can emit at wavelengths easily absorbed by water and blood, such as 980 nm and 1470 nm. Procedure is fast and can be done in the physician's office with little or no anesthesia used.

The above and other objects, features and advantages of the present invention will become apparent from the following description read in conjunction with the accompanying drawings.

DETAILED DESCRIPTION OF PREFERRED EMBODIMENTS

Present invention seeks to noninvasively treat patients with uterine growths such as polyps and myomas that may cause different types of complications to women, including discomfort, acute pain, anemia, inability to achieve or maintain pregnancy as well as problems with sexual activity and/or with menstruation.

Technique comprises accessing the inside of the uterus through the cervix, applying laser energy under direct vision to reduce or eliminate targeted, unwanted, uterine growths such that complications due to their presence no longer exist and have minimum possibility of recurring. Laser radiation is transported via an optical fiber to the site where growth is located. A hysteroscope is used to find the uterine growths and control the process by direct visual inspection. Then, a treatment optical fiber is inserted through one of hysteroscope's channels to where the unwanted growth is located. Energy is applied until uterine growth is completely vaporized or shrunk to a size/shape for easy mechanical removal.

Figure 1:
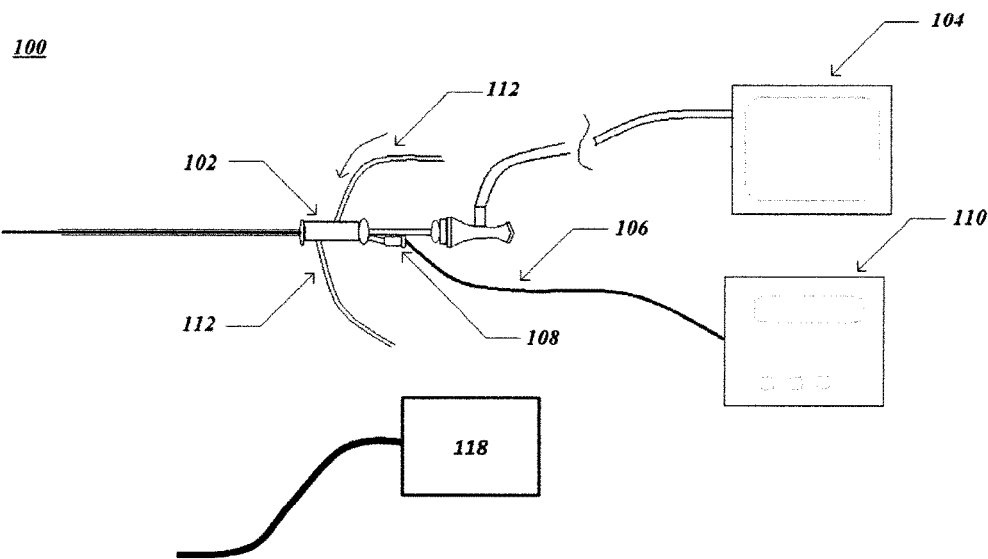
FIG. 1—shows main components of a preferred embodiment of present invention.
Figure 1:
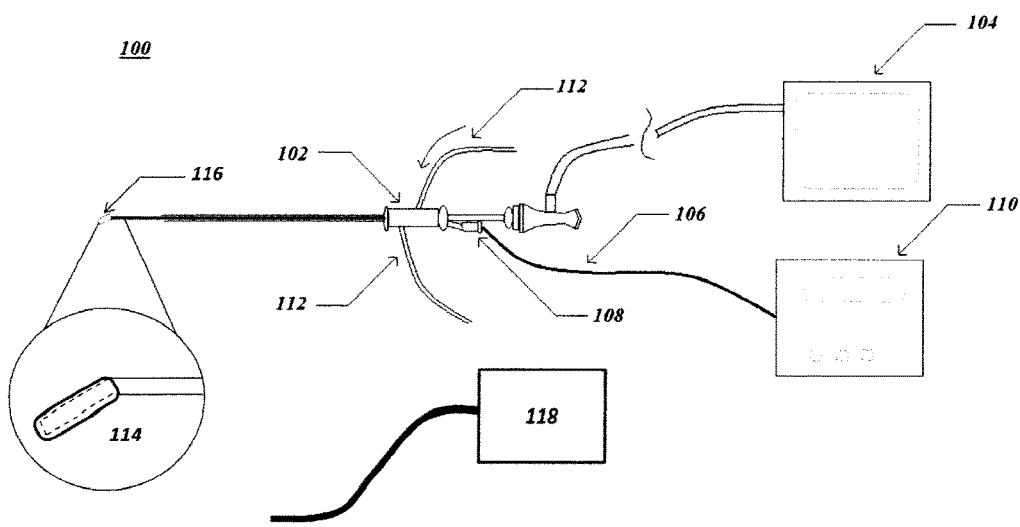
Figure 1:
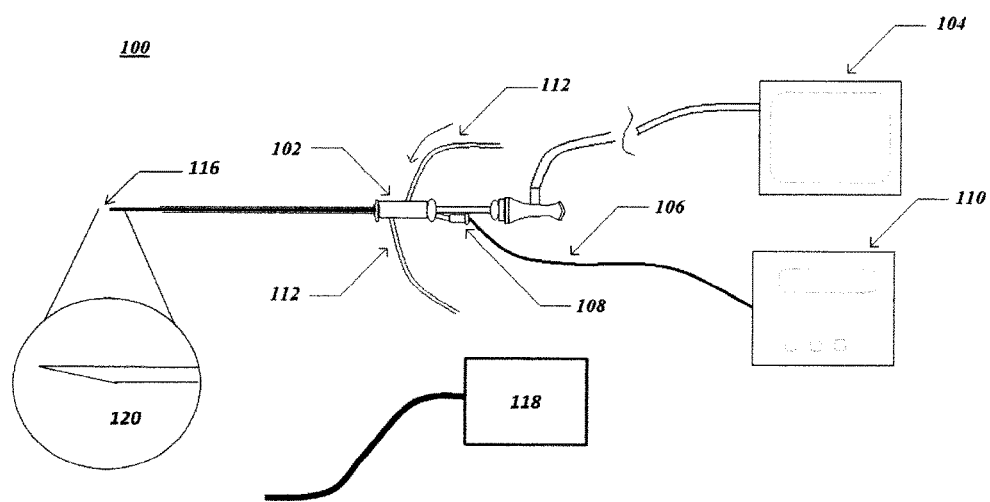

FIG. 1 depicts main components of a preferred embodiment of present invention. System 100 comprises an endoscope capable of accessing the uterus through the cervix (hysteroscope 102). Management of hysteroscope 102 is monitored on a video monitor 104. Hysteroscope 102 also accepts insertion of optical fiber 106 through fiber channel 108 conveying energy from laser source 110, and other channels such as an illumination channel (not shown) or irrigation channels 112 for clearing the surface of substances that prevent good vision. Irrigation channel 112 is also good for inserting a fluid to spread uterus open for easier access. In another preferred embodiment, spreading uterus open is achieved by injecting water absorbing polymers, such as commercially available WATCHSORB®, avoiding risks involved with water pressure and electrolyte loss. In preferred embodiments, hysteroscope 102, flexibility is such that viewing angle and direct energy emission can be oriented properly. Off axis emitting fibers 114 are preferred radiation distribution devices 116 for growths located on the inner wall of the uterus. If growth is located outside the uterus, a needle-like fiber 120 is a preferred radiation distribution device 116. In a preferred embodiment, emission of about 980 nm laser energy is applied. This wavelength is well absorbed by fibroid's water and blood content so procedure is efficient. This treatment can be applied to many types of uterine growths, including myomas, polyps and adhesions. Preferably, fiber size and design is chosen according to size, shape and location of target growth.

Figure 2:
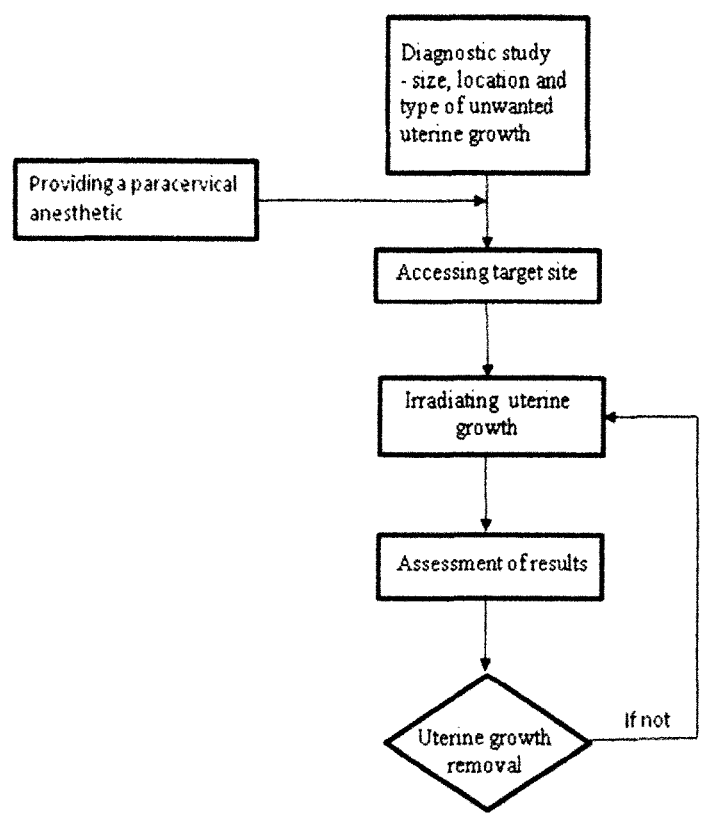
FIG. 2—shows main method steps of a preferred embodiment of present invention.

The main steps that comprise a preferred embodiment for treatment of myomas/fibroids are shown in FIG. 2 and summarized as follows: First of all, a diagnostic study is carried out comprising hysteroscopic direct viewing and vaginal ultrasound examination to determine, size, location and type of fibroids present according to Wamsteker classification. Next, an optical fiber is introduced and placed with emitting portion pointing towards target fibroid. Fiber tip may be placed very close to, touching or inside target tissue according to effect desired. Laser is applied until fibroid is shrunk and mechanically removed or vaporized completely. Laser wavelength is preferably 980±20 nm. In other embodiments, alternative wavelengths well absorbed by water or blood, the main components of soft tissue, are applied, including but not limited to 1470±60 nm, and 1950±50 nm. Treatment is repeated with other existing myomas. Finally, ultrasound imaging is employed to confirm success of procedure. Lasing procedure lasts a total of approximately 20 minutes, initially at a power of 50 W and then increased to 90 W.

A preferred hysteroscope for this procedure should have a small external diameter, adequate optics and very good imaging quality, and should have a working channel of at least 3 mm and therefore allow for the use of any laser fiber and the introduction of 7-French auxiliary instruments. One such hysteroscope, for example, has the following main features:

Outer Diameter: 17.5 French (5.8 mm).
Inner Diameter: 3.5 mm×4.04 mm.
Work channel: 3 mm (9 French).
Optics:
  Angle of vision: 12°.
  Visual Field: 90°.
  Optics diameter: 2.05 mm×3.63 mm.
  Length: 227 mm.

For uterine growths located on the inner wall of uterus, optical fiber is preferably designed with an off-axis distal end configuration, such as a bent tip fiber with a fused sleeve as an integral part of it placed at the fiber's distal end and with a rotatable connector at the proximal side. Such fiber has a core diameter between 400 and 500 µm and can fit through a 5 French working channel, and curved design at emitting end allows for working comfortably within the uterus cavity because of an easier access. The fiber allows for work at high power without significantly and progressively affecting its tip. Thus, work quality and speed are also not significantly diminished. Fiber tip offers a surface that allows for selective light vaporization of myoma's soft tissue at very high powers. Its curvature allows for better management, making procedure more precise and with better vision of what is being vaporized. Correct vision of target tissue is achieved with the help of a pilot beam that fiber has at its tip.

For uterine growths located on the outer wall of the uterus, optical fiber is preferably designed with a needle-like emitting end, such as a commercially available needle-like fiber; a Laser Interstitial Thermal Therapy (LITT) fiber. LITT fiber is introduced through hysteroscope as explained previously for growths located on the inner wall of the uterus. Then fiber is introduced through uterus wall and into the myoma found on the outside of the uterus. Then, laser energy is applied, coagulating tissue and vessels inside target growth, thus reducing its size and eventually denaturing it. This procedure eliminates the need of otherwise having to carry out a laparoscopic procedure.

Described technique allows for a high rate of success in elimination of complications and recovery of the uterus' normal functions. Since procedure is done under direct endoscopic vision, with real time monitoring, and with the application of energy with ideal lasing parameters and fiber tip configurations, the method is highly accurate. The probability of recurrence is, thus, very low. It is atraumatic, painless and quick and can be carried out in a physician's office.

Soft tissue has a high percentage of water content. Therefore laser energy must be well absorbed by water for tissue to be removed effectively. In the same manner, absorption in hemoglobin is essential for coagulation without carbonization and for good hemostasis. Thus, laser energy should also be well absorbed by hemoglobin. Preferably, laser source is a diode laser system capable of emitting up to 300 Watts. High powers emitted, through an off-axis fibers are ideal for vaporizing soft tissue with a wavelength of 980 nm without leaving scars and in record time.

The present invention is further illustrated by the following examples in which present invention is applied on patients with symptomatic submucous myomas classified as G0, G1 or G2. In all cases, patients are instructed to take hormone contraceptives one month before procedure and 10 mg of Diazepam and 600 mg of Ibuprofen one hour before procedure. In all cases, paracervical anesthesia is applied. Laser device for selective light vaporization is used with capacity to emit up to 300 W at a wavelength of 980 nm. An off-axis optical fiber is used, capable of conveying light energy of 300 W at a wavelength of 980 nm. Fiber also emits a pilot beam at fiber tip to help address visualization of treatment field. A standard hysteroscope is used with a working channel of 3 mm.

Example 1

32 Year Old Patient, Nulligravid, Consulting for Hypermenorrhea.

Submucous 25-30 mm type G2 myoma was diagnosed using ultrasound and hysteroscopic imaging. Selective myoma vaporization procedure is carried on target myoma using elements described in present invention. Laser power is set at 100-120 W. With the same fiber, target myoma can be previously cut into smaller parts before vaporizing, allowing for a faster, more effective treatment. Vaporization is carried out by placing fiber in contact with myoma, then applying a slight pressure on myoma while sliding fiber tip from left to right. Then fiber is advanced to another portion of myoma until myoma is completely vaporized. Due to the fact that the laser energy can penetrate up to 3 mm into tissue, total vaporization is not necessary. Remaining portions of up to 5 mm in diameter are necrosed by themselves. Total treatment time employed in hysteroscopic procedure was 26 minutes.

Example 2

47 Year Old Patient with 2 Normal Pregnancies Consulting for Menorrhea.

A 30 mm type G2 fundal submucous myoma was found using ultrasound and hysteroscopic imaging. Selective myoma vaporization procedure is carried on target myoma using elements described in present invention. Laser power is set at 100-120 W. Before vaporizing, laser energy is first used to cut myoma in half. This is done by advancing fiber tip while making 360-degree rotations. Then, myoma is further cut into smaller pieces. This is done with longitudinal movements on resulting semi-spheres. The amount of cutting into smaller pieces depends on the size of original myoma. Every time myoma is cut into smaller portions, each portion is also partially vaporized so they end up even smaller in size than the prior level. Resulting small portions can be removed with forceps. Total treatment time employed in hysteroscopic procedure was 26 minutes.

Example 3

40 Year Old Patient with 2 Deliveries, One Cesarean and One Ectopic, Consulting for Hypermenorrhea.

A 30 mm type G1 submucous myoma found using ultrasound and hysteroscopic imaging. Selective myoma vaporization procedure is carried on target myoma using elements described in present invention. Laser power is set at 100-120 W. Before vaporizing, laser energy is first used to cut myoma in half. This is done by advancing fiber tip while making 360-degree rotations. Then, for each resulting half, the intramiometrial portion is attacked to make a transversal cut of remaining portion, thus achieving a reduction of myoma layers as if an onion is peeled. Remaining fragments are removed with forceps. Total treatment time employed in hysteroscopic procedure was 30 minutes.

All treatments were done in-office with no need for general or regional anesthesia, as patients suffer little or no pain. Procedure lasts a total of less than one half hour. They are well tolerated by patients with minimum adverse effects. Recovery is immediate and there are no alterations to patients' normal life. With this treatment, G 0, G I, and G II type myomas can be treated and chances of recurrence are minimum.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for the laser treatment of uterine growths without the use of general or regional anesthetic consisting of the steps of:
   a. providing a paracervical anesthetic to a cervix;
   b. inserting a hysteroscope into a uterus;
   c. assessing size, location and type of unwanted uterine growth;
   d. placing a distal end of said hysteroscope to a position proximate to said uterine growth;
   e. inserting an optical waveguide, whose proximal end is connected to a radiation source and whose distal end comprises a radiation distribution device, into said hysteroscope, wherein said radiation distribution device comprises a needle-like fiber;
   f. advancing said distal end of said waveguide through said distal end of said hysteroscope to a predetermined point inside said uterine growth;
   g. irradiating said uterine growth with radiation from said radiation source so as to cut/vaporize said growth to cause reduction to a size/shape for easy mechanical removal or elimination by vaporization of said uterine growth, while not impairing a patient's fertility;
   h. assessing results by ultrasound imaging; and,
   i. repeating steps g. and h. until unwanted growth is removed.

2. The method for treatment of uterine growth according to claim 1, wherein said radiation source is a diode laser.

3. The method, for treatment of uterine growths according to claim 1, wherein said uterine growth is selected from the group consisting of a myoma, a polyp, and an adhesion.

4. The method for treatment of uterine growths according to claim 1, wherein said optical fiber has a core diameter of less than 600 µm.

5. The method for treatment of uterine growths according to claim 1, wherein said radiation has a wavelength chosen from the group of 980±20 nm, 1470±60 nm, and 1950±50 nm.

6. A method for the laser treatment of uterine growths, without the use of general or regional anesthetic, consisting of the steps of:
  a. providing a paracervical anesthetic to a cervix;
  b. insetting a hysteroscope into a uterus;
  c. assessing size, location and type of unwanted uterine growth;
  d. irrigating the uterus
  e. placing a distal end of said hysteroscope to a position proximate to said uterine growth;
  f. inserting an optical waveguide, whose proximal end is connected to a radiation source and whose distal end comprises a radiation distribution device, into said hysteroscope, wherein said radiation distribution device comprises a needle like fiber;
  g. advancing said distal end of said waveguide through said distal end of said hysteroscope to a predetermined point inside said uterine growth;
  h. irradiating said uterine growth with radiation from said radiation source so as to cut/vaporize said growth to cause reduction to a size/shape for easy mechanical removal or elimination by vaporization of said uterine growth, while not impairing a patient's fertility;
  i. assessing results by ultrasound imaging; and,
  j. repeating steps h. and i. until unwanted growth is removed.

7. The method for treatment of uterine growths according to claim 6, wherein said step of irrigating uterus is achieved by injection of a water-absorbing polymer.

* * * * *